US00PP11472P

United States Patent [19]

Fuess

[11] Patent Number: Plant 11,472

[45] Date of Patent: Aug. 1, 2000

[54] CHRYSANTHEMUM PLANT NAMED 'EMPIRE SAPPHIRE'

[76] Inventor: Janet S. Fuess, 22 Country Club Dr., New York Mills, N.Y. 13417

[21] Appl. No.: 09/221,672

[22] Filed: Dec. 28, 1998

[51] Int. Cl.[7] ..... A01H 5/00

[52] U.S. Cl. ..... Plt./287

[58] Field of Search ..... Plt./287, 292

*Primary Examiner*—Howard J. Locker

*Attorney, Agent, or Firm*—C. A. Whealy

[57] ABSTRACT

A distinct cultivar of Chrysanthemum plant named 'Empire Sapphire', characterized by its outwardly spreading and freely branching habit; formal decorative-type inflorescences that are about 3.75 to 4.25 cm in diameter; numerous attractive red purple ray florets; compact cushion habit; numerous inflorescences per plant; early flowering response; and excellent garden performance.

1 Drawing Sheet

BACKGROUND OF THE INVENTION

The present invention relates to a new and distinct cultivar of Chrysanthemum plant, botanically known as *Dendranthema grandiflora* and referred to by the cultivar name Empire Sapphire.

The new cultivar is a product of a planned breeding program conducted by the Inventor in New Hartford, NY. The objective of the breeding program is to create new garden-type Chrysanthemum cultivars having inflorescences with desirable inflorescence forms and floret colors and good garden performance.

The new cultivar originated from a cross made by the Inventor in 1995, of the *Dendranthema grandiflora* cultivar Empire Cheyenne, disclosed in U.S. Plant Pat. No. 8,973, as the female, or seed, parent with a proprietary seedling selection identified as B88-2 as the male, or pollen, parent, described as a deep purple formal decorative-type garden Chrysanthemum.

The cultivar Empire Sapphire was discovered and selected by the Inventor as a flowering plant within the progeny of the stated cross in a controlled environment in New Hartford, NY., in August, 1996. The selection of this plant was based on its desirable inflorescence form and floret color and excellent garden performance.

Asexual reproduction of the new cultivar by terminal cuttings taken in a controlled environment in New Hartford, NY., since October, 1996, has shown that the unique features of this new Chrysanthemum are stable and reproduced true to type in successive generations.

BRIEF SUMMARY OF THE INVENTION

The cultivar Empire Sapphire has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Empire Sapphire'. These characteristics in combination distinguish 'Empire Sapphire' as a new and distinct cultivar:

1. Outwardly spreading and freely branching habit.
2. Formal decorative-type inflorescences that are about 3.75 to 4.25 cm in diameter.
3. Numerous attractive red purple ray florets.
4. Compact cushion habit.
5. Numerous inflorescences per plant.

6. Early flowering response.
7. Excellent garden performance.

Plants of the new Chrysanthemum flower earlier than plants of the female parent, the cultivar Empire Cheyenne, under natural season conditions. In addition, plants of the new Chrysanthemum and the cultivar Empire Cheyenne differ in ray floret color.

Plants of the new Chrysanthemum can be compared to plants of the commercial cultivar, Empire Garnet, disclosed in U.S. Plant Pat. No. 9,936. In addition to a different ray floret color, plants of the new Chrysanthemum had slightly smaller inflorescences and flowered earlier than plants of the cultivar Empire Garnet in side-by-side comparisons conducted in New Hartford, NY.

BRIEF DESCRIPTION OF THE PHOTOGRAPH

The accompanying photograph illustrates the overall appearance of the new cultivar. The photograph a side perspective view of a typical flowering plant of 'Empire Sapphire'.

This photograph shows the colors as true as it is reasonably possible to obtain in colored reproductions of this type. Floret and foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in 20-cm containers in New Hartford, NY., under outdoor natural season conditions which approximate those generally used in commercial garden Chrysanthemum production. Measurements and comparisons were determined on Sep. 18, 1998 about mid-day under 4,000 foot-candles of light in New Hartford, NY.

Bontanical classification: *Dendranthema grandiflora* cultivar Empire Sapphire.

Commercial classification: Formal decorative-type garden chrysanthemum.

Parentage:

*Female or seed parent.*—*Dendranthema grandiflora* cultivar Empire Cheyenne, disclosed in U.S. Plant Pat. No. 8,973.

*Male or pollen parent.*—Proprietary seedling selection identified as B88-2 and described as a deep purple formal decorative-type garden Chrysanthemum.

Propagation:

*Type*.—Terminal tip cuttings.

*Time to rooting*.—Seven to ten days with soil temperatures of 21° C.

*Rooting habit*.—Fine, fibrous and well-branched.

Plant description:

*Appearance*.—Perennial herbaceous formal decorative-type garden Chrysanthemum. Inverted triangle. Outwardly spreading and mounding. Freely branching.

*Plant height*.—About 23 to 28 cm.

*Foliage description*.—Leaf arrangement: Alternate. Length: About 4.5 to 5.5 cm. Width: About 3 to 3.5 cm. Base: Attenuate. Margin: Palmate, five-lobed. Color: Mature foliage upper surface: 137A. Mature foliage lower surface: 137C.

Inflorescence description:

*Appearance*.—Formal decorative-type inflorescence form; fully double inflorescences without disc florets. Compact cushion habit. Inflorescences borne on terminals above foliage, arising from leaf axils. Ray florets arranged acropetally on a capitulum. One inflorescence per terminal with numerous inflorescences per plant.

*Flowering response*.—Under natural conditions, plants flower about September 10th in New Hartford, NY. Plants exposed to artificially manipulated daylength will flower about 7 weeks after start of long nyctoperiod treatments.

*Inflorescence size*.—Diameter: About 3.75 to 4.25 cm.

*Ray florets*.—Length: About 1.8 cm. Width: About 6 mm. Number of ray florets per inflorescence: About 298. Color, opened inflorescence: Upper surface: Red purple, 72C in center of floret; 66D towards margins. Lower surface: 75C.

*Reproductive organs*.—Androecium: None, no disc florets observed. Gynoecium: Present on both ray and disc florets.

Disease resistance: Resistance to known Chrysanthemum diseases has not been observed on plants grown under commercial production conditions.

Seed production: Seed production has not been observed.

It is claimed:

1. A new and distinct cultivar of Chrysanthemum plant named 'Empire Sapphire', as illustrated and described.

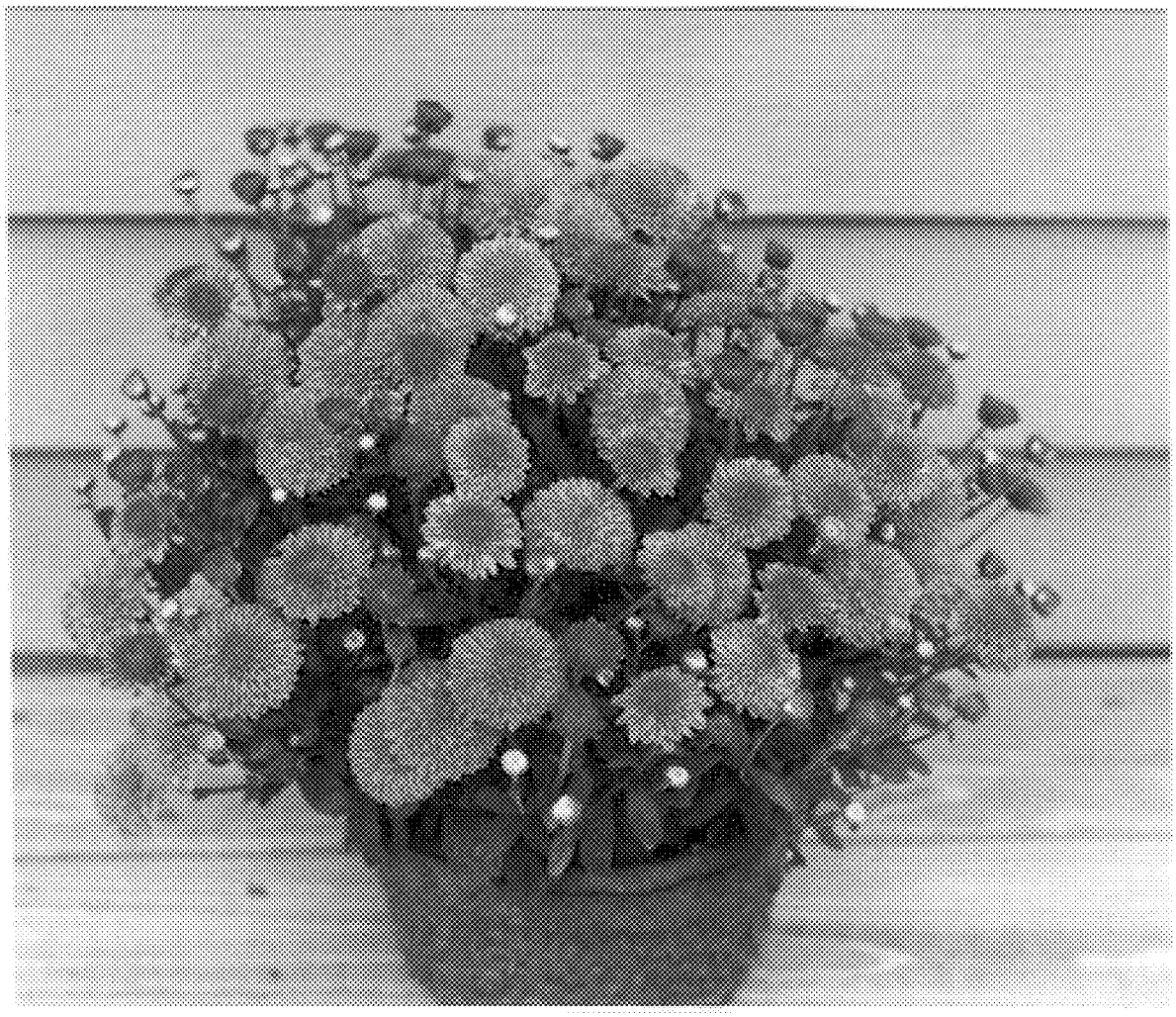

* * * * *